United States Patent [19]

Ponroy

[11] Patent Number: 6,069,138
[45] Date of Patent: May 30, 2000

[54] USE OF PHOSPHOLIPIDS OF ANIMAL ORIGIN IN THERAPY AND/OR DIETETICS

[76] Inventor: Yves Ponroy, 4A quai Ernest Ansermet, Montreux, CH-1820, Switzerland

[21] Appl. No.: 09/214,652
[22] PCT Filed: May 5, 1998
[86] PCT No.: PCT/FR98/00900
   § 371 Date: Jan. 21, 1999
   § 102(e) Date: Jan. 21, 1999
[87] PCT Pub. No.: WO98/50052
   PCT Pub. Date: Nov. 12, 1998

[30] Foreign Application Priority Data

May 6, 1997 [FR] France .................................. 97 05582

[51] Int. Cl.⁷ .................................................. A61K 31/685
[52] U.S. Cl. ............................................... 514/77; 514/78
[58] Field of Search ......................................... 514/77, 78

[56] References Cited

U.S. PATENT DOCUMENTS 5,449,683  9/1995  Wurtman .................................. 514/415

FOREIGN PATENT DOCUMENTS 0502765   9/1992  France .
0502766   9/1992  France .
WO9600016 1/1996  WIPO .
WO9600077 1/1996  WIPO .

*Primary Examiner*—Phyllis G. Spivack
*Attorney, Agent, or Firm*—Bierman, Muserlian and Lucas

[57] ABSTRACT

The invention concerns a novel use of phospholipids of animal origin in therapy and/or dietetics, more particularly the use of phospholipids rich in long-chain polyunsaturated fatty acids derived from animal brains or hen's eggs, to produce a pharmaceutical and/or dietetic composition to regulate melatonin secretion.

6 Claims, 6 Drawing Sheets

USE OF PHOSPHOLIPIDS OF ANIMAL ORIGIN IN THERAPY AND/OR DIETETICS

This application is a 371 of PCT/FR98/00900 filed May 5, 1998.

FIELD OF THE INVENTION

The present invention relates to a novel therapeutic and/or dietetic use of animal-derived phospholipids.

The present invention is more specifically directed to the use of phospholipids rich in polyunsaturated fatty acids for providing a pharmaceutical and/or dietetic composition which has an effect on melatonin secretion.

DISCUSSION OF THE PRIOR ART

Previous studies have suggested that melatonin, a neurohormone produced by the pineal gland, acts as an endogenous timing mechanism in humans (Armstrong—Melatonin: The internal Zeitgeber of Mammals. Pineal Res. Rev., 7: 157–202, 1989). Known pharmacological properties ascribed to melatonin mainly include its myorelaxant activity, sedative, hypnotic and tranquillizing effect (Sugden, D., Psychoparmacological effects of melatonin in mouse and rat—J. Pharmacol. Exp. Ther., 227, 587–591, 1983).

Melatonin alleviates immune deficiency induced by stress (Mestroni, Melatonin, Stress and the immune system. Pineal Res. Rev., 7: 203–206, 1989) and improves longevity, namely in mice.

Melatonin and its main liver metabolite—6-hydroxymelatonin—prevents experimental lipid peroxide formation in membranes—(R. J. Reiter, Antioxydant capacity of melatonin: a novel action not requiring a receptor—Neuroendocrinol. Let. 15, 103–116, 1993).

Recently, many investigators have incriminated the pineal gland and melatonin both in ageing process and ailments related to ageing. These theories derive from the important role melatonin plays in many biological functions and from the fact that melatonin production gradually declines in the living body with age (R. J. Reiter—The pineal gland and melatonin in relation to aging; Exper. Geront., 30: 199–212, 1995).

Several clinical trials have been undertaken to check the efficiency of melatonin in humans (R. Wurtman, Effects of melatonin on humain mood and performance, Brain Research, 323: 201–207, 1984; R. Brook, A double blind trial of melatonin as a treatment for jet lag, Biol. Pyschiatry, 33: 526–530, 1993).

Other studies were conducted to ascertain the influence of melatonin on the course of Alzheimer's disease (C. P., Maurizi, The mystery of A's D and its prevention by melatonin).

Chronic use of melatonin is a controversial issue even though intake of this hormone is apparently not harmful. It is however interesting to study the regulation of melatonin production by the pineal gland, particularly by food supply.

It has been shown that the n-3 fatty acid content of the pineal gland can be severely diminished in animals kept on an α-linolenic acid (18:n-3) deficient diet.

The most drastic change occurs for phospholipid glycerides in which the level of 22:6 n-3 fatty acids is reduced from 10.14% to 2.33%. In this situation, the cultured rat pineal gland's activity is lower as measured by melatonin release in the medium (N. Sarda, Effect of a n-3 fatty acid-deficient diet in melatonin release in cultured rat pineal. J. of Neurochemistry, 61: 1057–1063, 1993).

Arachidonic acid (20:4 n-6) and docosahexaenoic acid or DHA (22:6 n-3) are the main polyunsaturated fatty acids of the pineal gland. Both fatty acids account for nearly 25% of total lipids. They may exist as triglycerides in fish oil or as animal-derived phospholipids as found in brain and eggs.

Various experiments have demonstrated that animal-derived phospholipids form the finest food supplements of DHA and arachidonic acid for a great number of uses. It is quite relevant in this regard that phospholipids are themselves the building blocks of biological membranes.

Accordingly, the applicant has already disclosed in its previous patents, EP 502 766, EP 502 765, FR 2 714 574 and in European patent applications EP 95 923 373 and EP 95 923 374, phospholipids used for dietetic and therapeutic purposes.

SUMMARY OF THE INVENTION

An object of the present invention relates to the use of phospholipids rich in long chain-polyunsaturated fatty acids derived from animal brains or hen's eggs for the manufacture of a pharmaceutical and/or dietetic composition intended to regulate melatonin secretion.

DETAILED DESCRIPTION OF THE INVENTION

Long chain polyunsaturated fatty acids are those mainly found in the pineal gland, viz. arachidonic acid (20:4 n-6) and docosahexaenoic acid or DHA (22:6 n-3).

Phospholipids are combined with non toxic pharmaceutically acceptable excipients, extenders or inert carriers in order to make pharmaceutical and/or dietetic compositions for oral or parenteral administration.

Excipients or extenders suitable for such administration routes could be mineral products such as, for example, calcium carbonate, tricalcium phosphate, magnesium phosphate, alumina, colloidal silica, kaolin, clay, aluminium silicate, calcium silicate and iron oxide for oral administration, water or aqueous fluids for parenteral administration.

Inert carriers can be of organic origin such as starch, dextrins, lactose, celluolose, synthetic cellulose derivatives, alginates, carragheenans, casein salts, fatty acids, waxes or resins.

Phospholipids may further be combined with other accessory active ingredients such as vitamins, trace elements or mineral salts.

Vitamins may belong to the B complex, such as, for example, vitamin B1, vitamin B2, vitamin B6, folic acid, panthotenic acid, dihydrofolic acid, vitamin PP. Trace elements are exemplified by selenium, lithium, rubidium and mineral salts include for example magnesium salts.

Compositions according to the invention are provided as oral ampuls, vials, soft gelatine capsules, hard capsules, coated or uncoated tablets, troches, pasta, granulates and flavored or unflavored powders having a sweetener added or not.

Compositions may also be provided in liquid dosage forms such as for example gel-like preparations or oral suspensions or still, oil-in-water emulsions.

Phospholipids are administered in a quantity of 10 to 300 mg per dosage unit.

Figure 1:
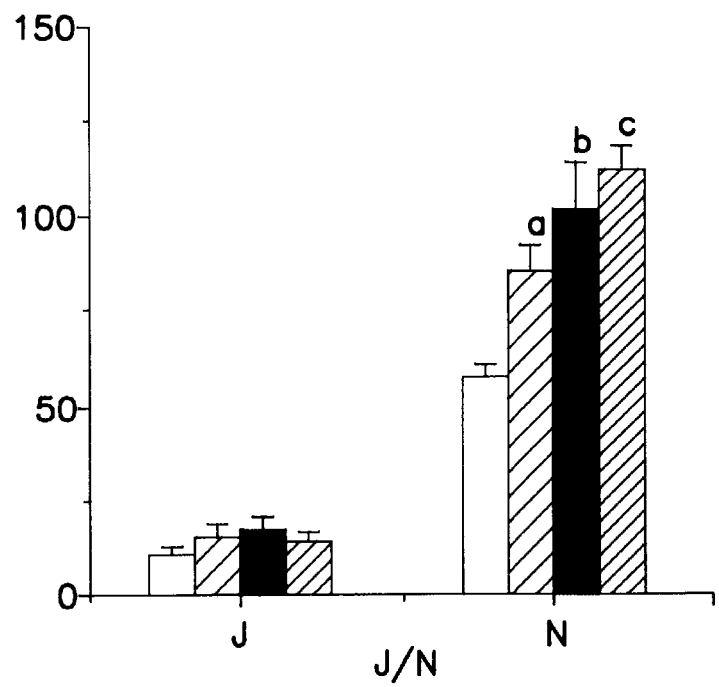
FIG. 1 is a graph of different nutritional regimes of urine excretion over 5 weeks.

Phospholipids of the present invention are used to manufacture a pharmaceutical and/or dietetic composition in order to improve the quality of nightime sleep, alertness during the day, as well as memory and learning skills.

The foregoing non limiting examples and experiments are intended to further describe the present invention.

EXAMPLE I

Preparation of a composition based on high arachidonic acid and DHA content phospholipids, extracted from mammal brains.

| | |
|---|---|
| Brain-derived phospholipids | 10–300 mg |
| concentrated wheatgerm oil | 10–100 mg |
| lactose | 50–200 mg |
| tricalcium phosphate | 10–100 mg |
| caseinates | 15–50 mg |
| Magnesium bromide | 5–20 mg |
| | per one soft capsule |

EXAMPLE II

Soft gelatine capsules based on high arachidonic acid and DHA content brain phospholipids.

| | |
|---|---|
| Brain-derived phospholipids | 10–300 mg |
| Vitamin B1 | 0.7–4.2 mg |
| Vitamin B2 | 0.8–4.8 mg |
| Vitamin B6 | 0.5–5 mg |
| Folic acid | 100–600 mg |
| Lactose | 50–200 mg |
| Magnesium stearate | 5–30 mg |
| Colloidal silica | 5–25 mg |
| | per one soft capsule |

The following experiment demonstrates the therapeutic use of animal-derived phospholipids in accordance with the invention, viz. melatonin secretion regulation.

Pharmacological Testing and Therapeutic Applications of Phospholipids According to the Invention 1—Tests The animal-derived phospholipids are extracted, by means of appropriate solvents, either from swine brain or hen's eggs, which animals have been kept on a special diet enriched with fatty acids of the n-3 series.

Phospholipid extraction procedures and conditions have been respectively described in the european patent applications N° 95 923 373 (extraction from hen's eggs) and N° 95 923 374 (extraction from swine brains).

Final products herein contain common phospholipid types; however, proportions thereof vary according to the source of materials.

| Phospholipid type | Brain phospholipids | Egg phospholipids |
|---|---|---|
| Sphingomyelin | 5–10% | |
| Phosphatidylcholine | 20–30% | 70% |
| Phosphatidylserine | 15–20% | 5% |
| Phosphatidylinositol | 3–5% | |
| Phosphatidylethanolamine | 30–40% | 16% |
| Phosphatidic acid | 3–5% | 2% |
| Lysophospholipids | 2–10% | 2–5% |

When hens are fed on a normal diet, the fatty acid content is substantially equal between brain phospholipids and hen's egg phospholipids (see the following table).

| Fatty acids | Brain phospholipids | Egg phospholipids |
|---|---|---|
| Saturated fatty acids | 37.5% | 40% |
| Monounsaturated fatty acids | 37.6% | 30% |
| Polyunsaturated fatty acids (n – 6) | 15% | 19% |
| Arachidonic acid | (4–5%) | (4–5%) |
| Polyunsaturated fatty acids (n – 3) | 10% | 9% |
| Eicosapentaenoic acid (EPA) | (0.3%) | (0.4%) |
| Docosahexaenoic acid (DHA) | (9%) | (8%) |

2—Animal testing

Experimental procedure a) Animals and Animal Diets 4 animal groups were studied:

Groups 1 & 2

Groups 1 and 2 were comprised of Wistar rats. These rats were fed for two generations on a diet containing 6% of a (60/40) mixture of peanut oil and rapeseed grains (this group is referred to as "control group" or "rapeseed grains" or exclusively composed of peanut oil (this group is referred to as "n-3 deficient" or "peanut" group).

The diet on which the control group is maintained is balanced with respect to 18:2n-6 and 18:3n-3 fatty acids.

Groups 3 & 4

Groups 3 and 4 are comprised of weaned, 21 day-old rats, with corresponding mother rats being included in the control group ("rapeseed grains") or n-3 deficient group ("peanut"). These rats were maintained on a diet supplemented with animal-derived phospholipids ("PL") and enriched with n-3 fatty acids so as to achieve a 200 mg of n-3 fatty acid intake per 100 g of food for deficient animals (this group is referred to as n-3+PL-deficient group or "peanut"+PL-); a 400 mg of n-3 fatty acid intake per 100 g of food for control rats (this group is referred to as control group+PL-or "rapeseed"+PL-).

The rats were kept on this diet till the end of the experiment.

b) Urine Sampling

Animals were maintained in a well controlled environment (screened light; temperature equal to 21±1° C.; food and drink ad lib) upon entering a metabolism-monitoring cage. Stress due to isolation requires an adaptation period of 5 days: thus, no sample was withdrawn during this period, however the consistency of urine volume is checked. After this 5 day interval, urine samples were taken from each rat.

c) Results

Pineal gland fatty acid assay shows significant differences between individual groups regarding n-3 fatty acids and especially for DHA.

TABLE I

Phospholipid supplementation (PL) results in a significant increase in 22:6 n − 3 fatty acid level.

|  | "rapeseed grain" Control group | "peanut" n − 3 deficient group | Control group + animal phospholipids | n − 3 deficient groupe + animal phospholipids |
|---|---|---|---|---|
| 22:6 n − 3 | 7.2% | 1% | 10.6% | 11.3% |
| Σn − 3 | 8.5% | 1.2% | 12% | 12.3% |
| n−6 / n − 3 | 3.1% | 27.3% | 2.2% | 2.1% |
| 20:4n−6 / 22:6n − 3 | 1.83% | 15.3% | 1.3% | 1.3% |

In these animals, nightime melatonin secretion has been found to decrease by 32% in the n-3 deficient group with respect to the control group. By contrast, the intake of phospholipids from animal origin results in 75.8% increase in melatonin excretion in urine as compared to the n-3 deficient group and in 31% increase with respect to the control group.

FIG. 1 shows the effects of different nutritional regimens on sulfatoxy-melatonin excretion in urine, in rats during daytime (J) and nightime cycles (N) based on two consecutive night measurements over 5 weeks.

The J/N ratio is plotted on the abscissa axis, the quantity of sulfatoxy-melatonin excreted in urine during 12 hours expressed in mg is plotted on the ordinate axis.

Rectangles with grey dots  represent the n-3 deficient "peanut" group, partially hatched rectangles  represent the "rapeseed grain" control group, crosshatched rectangles  stand for the n-3 deficient "peanut" group supplemented with animal phospholipids, and fully hatched rectangles  stand for the "rapeseed grain" control group supplemented with animal phospholipids.

(a): $p<0.01$ "rapeseed grains" with respect to "peanut'
(b): $p<0.01$ "peanut"+PL with respect to "peanut"
(c): $p<0.01$ "rapeseed grains"+PL with respect to "rapeseed grains".

d) Conclusion

These data show on one hand that phospholipid intake can correct n-3 fatty acid deficiency at the pineal level and that the intake of phospholipids rich in polyunsaturated fatty acids potentiates the production of melatonin on the other hand.

3—Study of Brain Phospholipid Effects on Poor Sleepers a) Experimental Conditions The following experiment was conducted on 24 healthy subjects of both sexes complaining of poor sleep with a mean age of 30.3 years. These subjects had to fulfil two conditions at least out of four.

sleep onset time: >20 minutes
nightime wake-up periods: ≧60 minutes
number of nightime wake-up events: 4
sleep duration: ≦6H30

These criteria were shown during two polygraphic recordings for two consecutive nights. These polygraphic recordings were visually rated according to Rechtschaffen and Kale's method of scoring.

Double blind parallel studies were conducted for 9 weeks by administering a daily dose of 4 soft gelatine capsules to two perfectly matched groups divided according to the random distribution table of Cochran and Cox.

Group A: 15 mg of brain phospholipids per soft gelatine capsule

Group B: placebo

Each subject has to keep a daily written record of his sleep according to 3 analogic scoring charts relative to sleep onset time, state of vigilance at time of wake-up, sleep duration and finally to fill a questionnaire delivered by the hospital staff.

b) Results

Group A members reported they have experienced deeper sleep than group B subjects.

Figure 2:
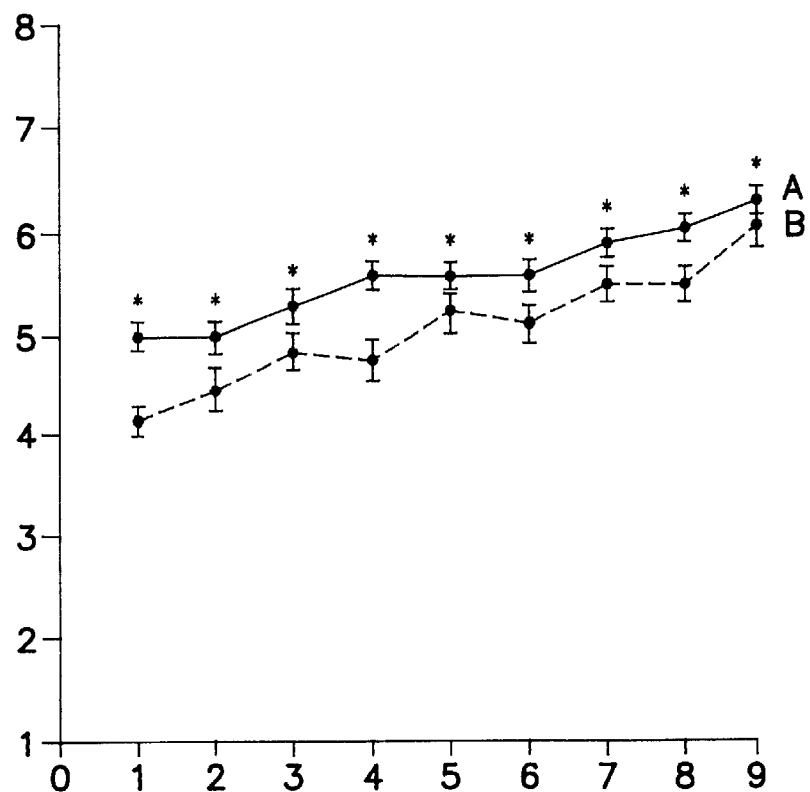
FIG. 2 is a graph of sleep depth grades in 2 groups.

FIG. 2 shows the sleep depth grades in groups A & B.

The abscissa axis shows the number of weeks while the ordinate axis shows sleep depth grades.

Group A subjects reported wake-up events were less frequent (between 0 and 1) than group B subjects (between 1 and 2).

Figure 3:
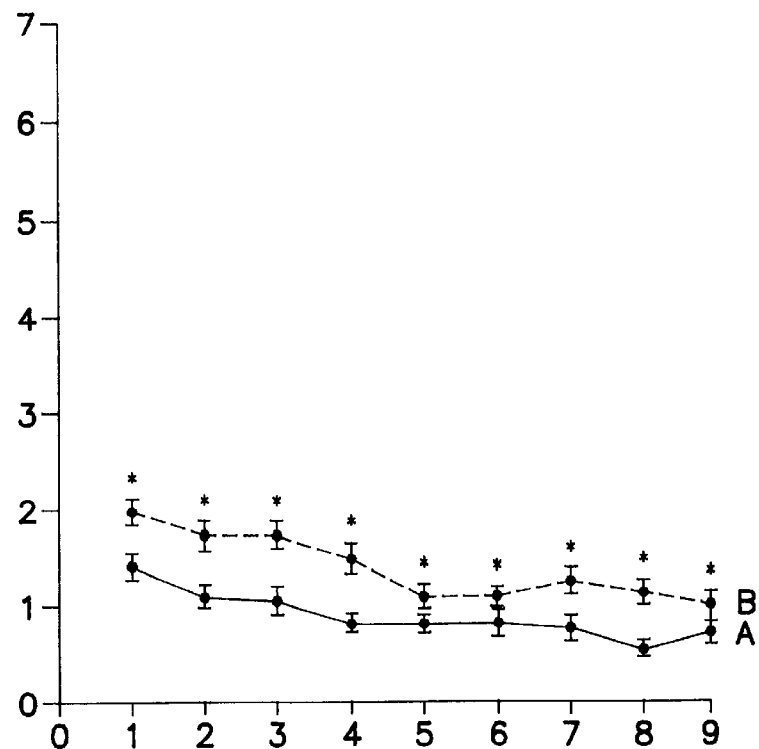
FIG. 3 is a graph of the number of night time wake ups of 2 groups.

FIG. 3 illustates the number of nightime wake-up events for both groups A and B. The abscissa axis values represent the number of weeks whereas the ordinate axis values correspond to the number of nightime wake-up events.

Group A subjects also observed that they spent less time being sleepless during the night than group B subjects.

Figure 4:
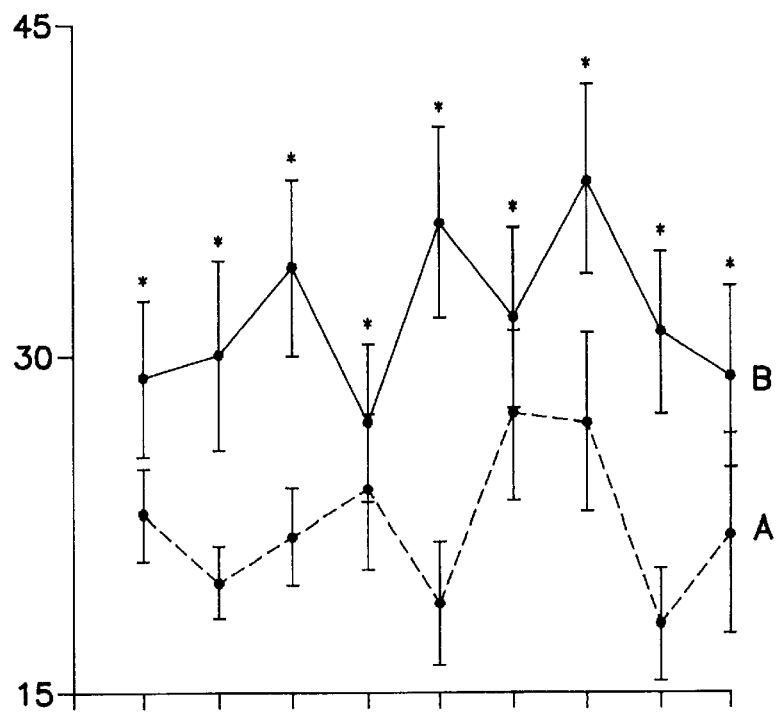
FIG. 4 is a graph of the duration of night time wake ups of 2 groups.

FIG. 4 shows the duration of night wake-up events for both groups A and B. The abscissa axis gives the number of weeks whereas the ordinate axis gives the duration of night wake-up events (in minutes).

Total sleep time increased significantly for group A (445 minutes±29 minutes of sleep time) relative to group B (362 minutes±28 minutes of sleep time).

Figure 5:
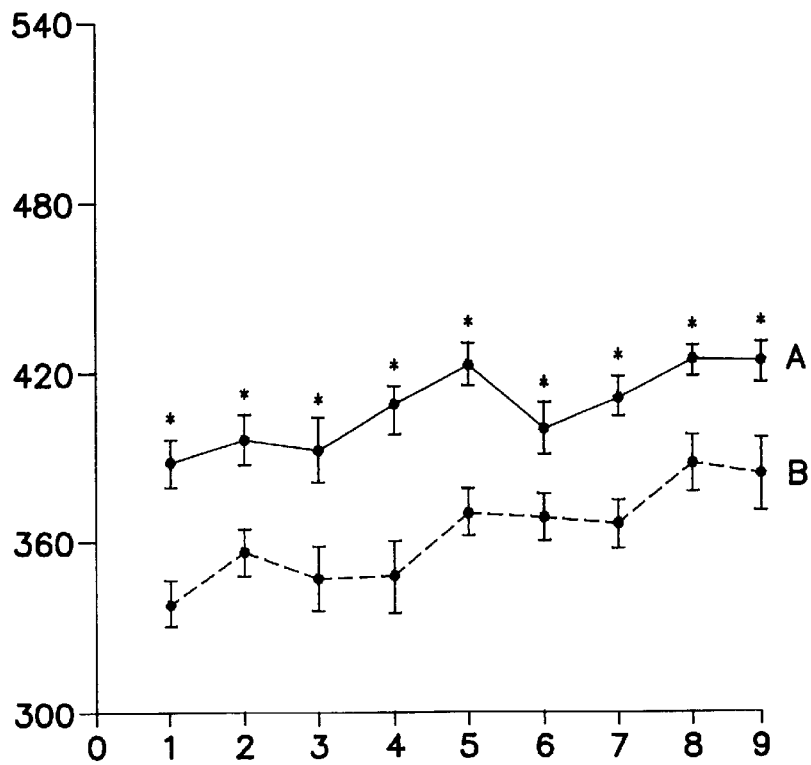
FIG. 5 is a graph of total sleep time for 2 groups.

FIG. 5 shows total sleep time for both groups A and B.

Abscissa axis gives the number of weeks whereas the ordinate axis gives the total sleep time (in minutes).

The number of drowsiness and snoozing events during daytime was higher for group B than group A.

Figure 6:
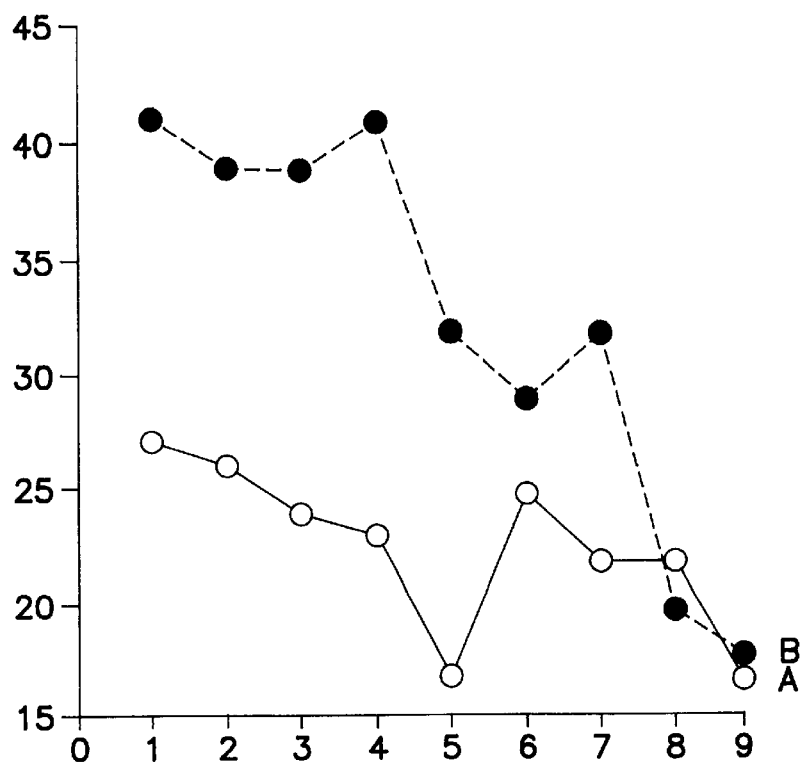
FIG. 6 is a graph of the number of time of drowsiness for 2 groups.

FIG. 6 shows the number of times drowsiness was experienced for groups A and B. The abscissa axis represents the number of weeks whereas the ordinate axis represents the number of times where drowsiness was experienced.

c) Conclusion

These results demonstrate the beneficial effect of brain phospholipids on the quality of sleep and sleep time as well as alertness level during daytime.

4—Study During Daytime of the Psychomotor Performances of Poor Sleepers a) Experimental conditions This study was conducted in a university hospital facility dedicated to sleep investigation. 16 poor sleepers were selected for the study and divided into two fully homogenous groups.

Both groups were administered 4 capsules daily for a period of 2 months containing either product A (15 mg of brain phospholipids per capsule) or product B (placebo). The subjects were submitted to a series of psychomotor tests at days 1, 15, 43 and 57. Data were examined for statistical significance using the variance analysis method (ANOVA).

b) Results

Attention Focusing Test (Computer-Assisted)

Mean reaction time was significantly increased in group A.

The number of errors significantly increased (p=0.0005) in group B (4.58) in relation to group A (2.48).

Figure 7:
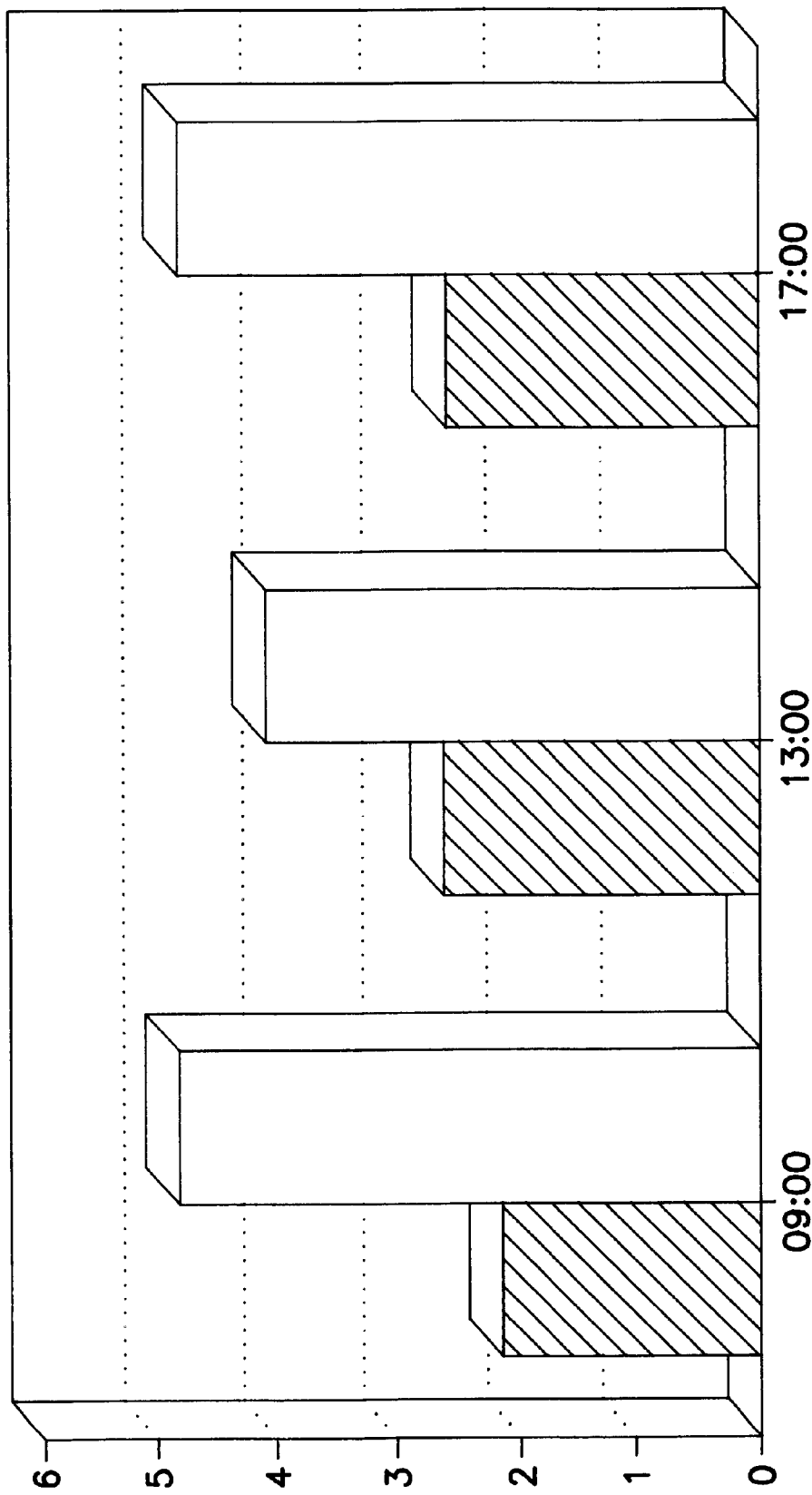
FIG. 7 is a graph of an attention focusing test.

FIG. 7 shows the attention focusing test.

Hatched rectangles represent group A and white rectangles stand for group B (placebo).

The abscissa axis shows the time in hours at which the test was performed and the ordinate axis shows the number of errors.

Manual Skill Test

This test demonstrates that brain phospholipids improve performance in the most complex test of visual-motor coordination (assembling) but are not effective when testing very easy tasks.

Symbol Cross-Matching Test

The proportion of symbols correctly cross matched increased significantly in group A, with no effect being observed on speed performance.

Verbal Auditive Learning Test

The number of words memorized is greater in group A (79.96%) than in group B (75.64%)

Learning speed is much higher in group A (4.76) than in group B (5.54).

Figure 8:
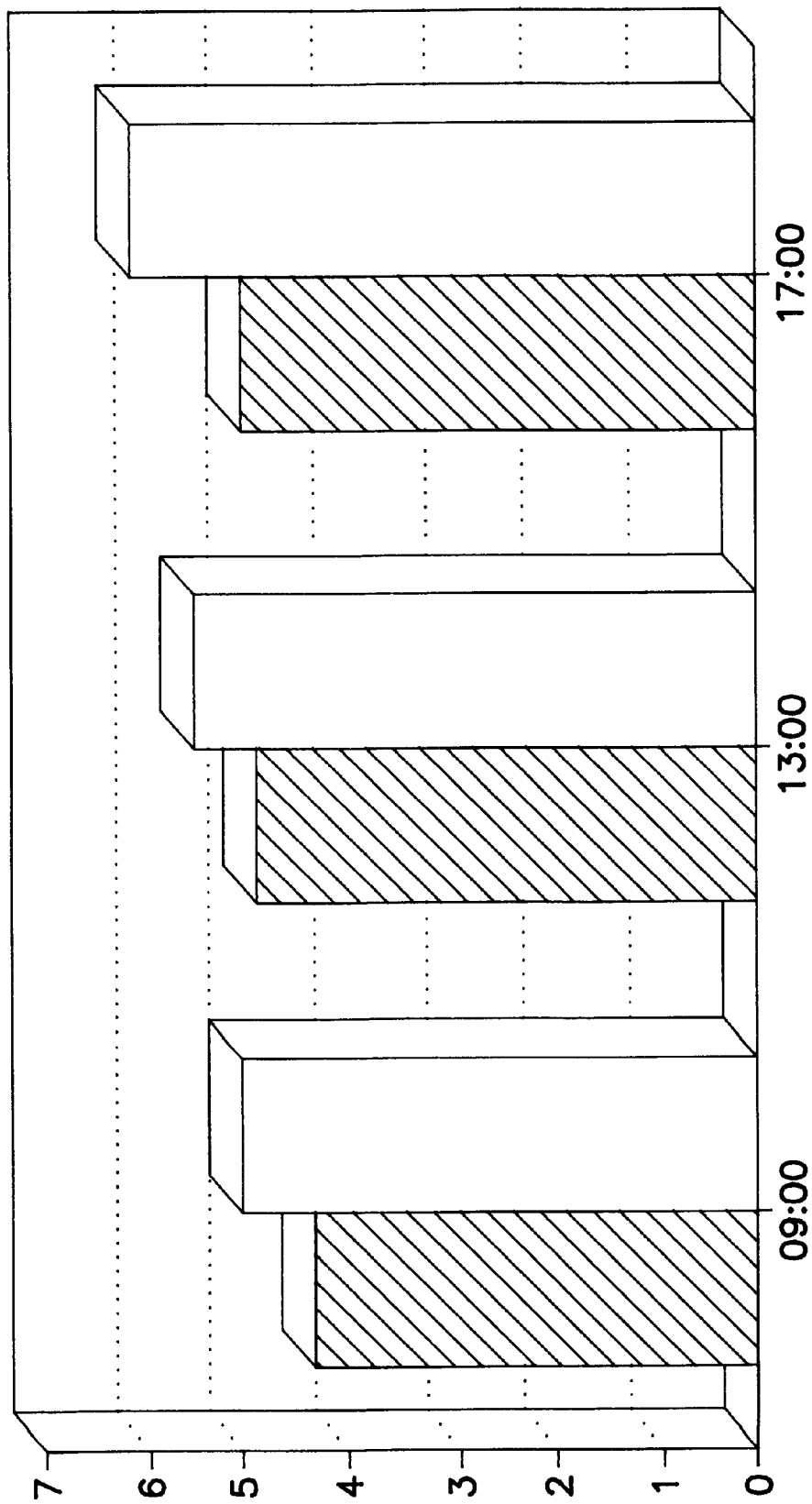
FIG. 8 is a graph of learning speed for 2 groups.

FIG. 8 shows learning speed in groups A and B.

Group A is represented by hatched rectangles while group B (placebo) is shown by white rectangles.

The abscissa axis shows the time in hours at which the test was conducted and the ordinate axis shows the learning speed.

The number of errors is significantly decreased in group A (0.56) with respect to group B (1.82).

Figure 9:
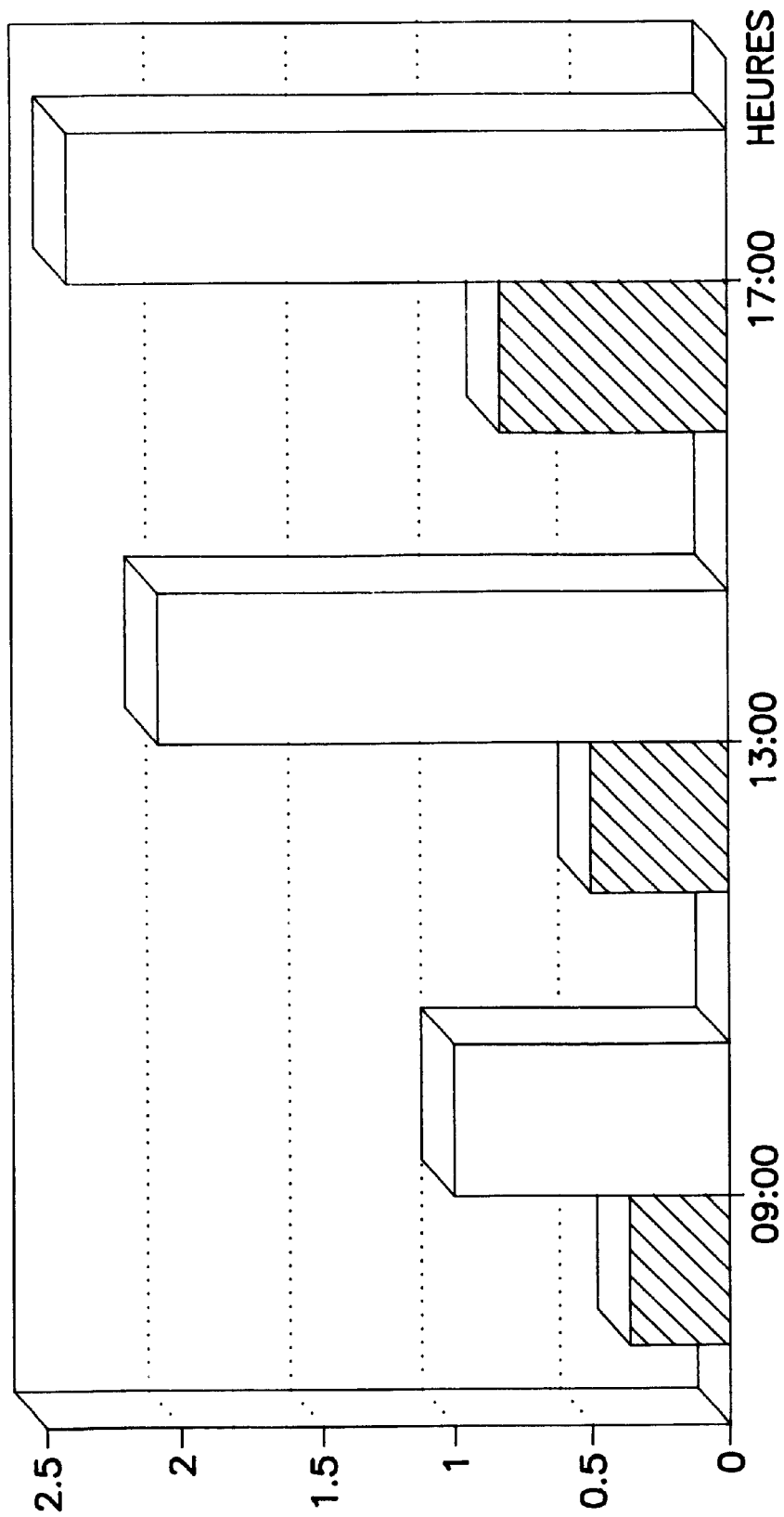
FIG. 9 is a graph of the number of errors in 2 groups.

FIG. 9 shows the number of errors in groups A and B.

Group A is shown by hatched rectangles and group B (placebo) is shown by white rectangles.

The abscissa axis shows the time in hours at which the test was conducted and the ordinate axis shows the number of errors.

From these results, it can be concluded that brain phosholipids result in significant improvement of learning and memory skills, correlated with higher secretion of melatonin.

Numeral Series Test

This test consists in repeating a series of figures as long as possible. There is no significant difference between the two groups.

Delayed Visual Recognition Test

The number of recognized objects does not differ between both groups.

It can thus be concluded that the intake of brain phospholipids improves memory performance related to learning and memorization skills.

These results are consistent with the previous study which has shown that sleep quality is enhanced and that daytime attention is improved.

These data offer a clear understanding of the effects on learning skills.

These experimental studies confirm that the intake of phosholipids rich in DHA and arachidonic acid derived from mammal brains or eggs from properly fed hens, induce the secretion of melatonin, finally resulting both in improving the quality of sleep and improving the learning skills.

The pharmaceutical and/or dietetic compositions of the present invention, intended to regulate melatonin secretion, are particularly adapted to the elderly and poor sleepers for whom a nightime diminished plasma concentration of melatonin is usually observed.

The pharmaceutical and/or dietetic compositions of the present invention have most notably beneficial effects on sleep and sleep quality, wake-up and attention, mood, learning and memory performance.

Owing to the antioxidant effect of melatonin and its free radical scavenger activity, the pharmaceutical compositions of the present invention can further be used to slow down ageing processs. Alzheimer's disease is a case of special interest. In this disease, the nightime secretion of melatonin is virtually absent.

What is claimed is:

1. A method of regulating melatonin secretion in warm-blooded animals comprising administering to warm-blooded animals in need thereof an amount of phospholipids having a high content of long chain polyunsaturated fatty acids derived from animal brains or hen's eggs sufficient to regulate melatonin secretion.

2. The method of claim 1 wherein the phospholipids have a high content of arachidonic acid (20:4 n-6) and docosahexaenoic acid or DHA (22:6 n-3).

3. The method of claim 1 wherein the phospholipids are admixed with at least one vitamin.

4. The method of claim 1 wherein the phospholipids are admixed with at least one trace element.

5. The method of claim 1 wherein the phospholipids are admixed with at least one mineral salt.

6. The method of claim 1 wherein the phospholipids are administered in a quantity of 10 to 300 mg per unit dosage.

* * * * *